United States Patent
Yamada et al.

(10) Patent No.: US 9,814,238 B2
(45) Date of Patent: Nov. 14, 2017

(54) HERBICIDE COMPOSITION

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 15/027,472

(22) PCT Filed: Oct. 17, 2014

(86) PCT No.: PCT/JP2014/077735
§ 371 (c)(1),
(2) Date: Apr. 6, 2016

(87) PCT Pub. No.: WO2015/060221
PCT Pub. Date: Apr. 30, 2015

(65) Prior Publication Data
US 2016/0242417 A1    Aug. 25, 2016

(30) Foreign Application Priority Data
Oct. 23, 2013 (JP) ................................ 2013-220680

(51) Int. Cl.
*A01N 43/54* (2006.01)
*A01N 47/36* (2006.01)

(52) U.S. Cl.
CPC ............ *A01N 47/36* (2013.01); *A01N 43/54* (2013.01)

(58) Field of Classification Search
CPC combination set(s) only.
See application file for complete search history.

(56) References Cited

U.S. PATENT DOCUMENTS

| | | |
|---|---|---|
| 2002/0004457 A1 | 1/2002 | Nevill et al. |
| 2004/0235665 A1 | 11/2004 | Zagar et al. |
| 2005/0090396 A1 | 4/2005 | Feucht et al. |
| 2008/0254985 A1 | 10/2008 | Zagar et al. |
| 2011/0224083 A1 | 9/2011 | Ko et al. |
| 2014/0121108 A1 | 5/2014 | Yamada et al. |

FOREIGN PATENT DOCUMENTS

| | | |
|---|---|---|
| EP | 2343284 A2 | 7/2011 |
| JP | 2002-529379 A | 9/2002 |
| JP | 2005-502715 A | 1/2005 |
| JP | 2005-510577 A | 4/2005 |
| JP | 2009-511538 A | 3/2009 |
| JP | 2012/504599 A | 2/2012 |
| JP | 2012-229202 A | 11/2012 |
| WO | 2011/018486 A2 | 2/2011 |
| WO | 2013/154396 A1 | 10/2013 |

OTHER PUBLICATIONS

Flazasulfuron 25WG label, obtained from the internet on Mar. 18, 2017: <https://www3.epa.gov/pesticides/chem_search/ppls/071512-00012-20080702.pdf>, Apr. 21, 2011.*
Mesch, P. et al., "Trifloxysulfuron-sodium: a new post-emergence herbicide for use in Australian cotton and sugarcane," Proceedings of the Australian Weeds Conference, vol. 13, pp. 345-347 (2002).*
Rummens, F.H.A., "An improved definition of synergistic and antagonistic effects," Weed Science, vol. 23 (1), pp. 4-6 (1975).*
Richer, D.L., "Synergism—a patent view," Pesticide Science, vol. 19, pp. 309-315 (1987).*
Colby, S.R., "Calculating synergistic and antagonistic responses of herbicide combinations," Weeds, vol. 15, pp. 20-22 (1967).*
International Search Report issued with respect to application No. PCT/JP20141077735, dated Jan. 13, 2015.
International Preliminary Report on Patentability issued with respect to application No. PCT/JP20141077735, dated Apr. 26, 2016.

* cited by examiner

*Primary Examiner* — John Pak
(74) *Attorney, Agent, or Firm* — Greenblum & Bernstein, P.L.C.

(57) ABSTRACT

To provide a high active herbicidal composition to control undesired plants represented by weeds to be controlled.
A herbicidal composition comprising tiafenacil or its salt and flazasulfuron or its salt.

7 Claims, No Drawings

HERBICIDE COMPOSITION

TECHNICAL FIELD

The present invention relates to a herbicidal composition and a method for controlling undesired plants.

BACKGROUND ART

Patent Document 1 discloses uracil compounds of the formula (I) including tiafenacil, and discloses that they may be used as mixed with other herbicides. Further, Patent Document 2 discloses a herbicidal composition comprising an uracil compound of the formula (1) including tiafenacil and a herbicidal compound.

However, Patent Document 1 failed to specifically disclose a combination of (A) tiafenacil and (B) flazasulfuron. Further, it failed to disclose a synergistic herbicidal effect obtained when they are combined. Further, Patent Document 2 failed to disclose flazasulfuron.

PRIOR ART DOCUMENTS

Patent Documents

Patent Document 1: European Patent Publication No. 2343284
Patent Document 2: WO2013/154396

DISCLOSURE OF INVENTION

Technical Problem

At present, many herbicidal compositions have been developed and used, but they are not necessarily sufficient for controlling undesired plants represented by weeds to be controlled, and a high active herbicidal composition has been desired.

The object of the present invention is to provide a herbicidal composition comprising a combination of two active ingredients, which has activity higher than the respective herbicidal activities of the two active ingredients, and a method for controlling undesired plants, which comprises using the composition.

Solution to Problem

The present inventors have conducted extensive studies and found that a high active herbicidal composition can be obtained by combination of specific compounds, and accomplished the present invention.

That is, the present invention relates to a herbicidal composition comprising as active ingredients (A) tiafenacil or its salt (hereinafter referred to as compound A) and (B) flazasulfuron or its salt (hereinafter referred to as compound B). The present invention further relates to a method for controlling undesired plants or inhibiting their growth, which comprises applying a herbicidal composition comprising as active ingredients compound A and compound B to the undesired plants or to a place where they grow. The present invention still further relates to a method for controlling undesired plants or inhibiting their growth, which comprises applying a herbicidally effective amount of compound A and a herbicidally effective amount of compound B to the undesired plants or to a place where they grow.

Advantageous Effects of Invention

According to the present invention, it is possible to provide a high active herbicidal composition.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E = \alpha + \beta - (\alpha \times \beta \div 100)$$

where $\alpha$: growth inhibition rate when treated with x (g/ha) of herbicide X,
$\beta$: growth inhibition rate when treated with y (g/ha) of herbicide Y,
E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

Compound A or compound B may form a salt, an isomer or the like, and they are all included in the present invention so long as they are agriculturally acceptable.

As for compound A, tiafenacil (common name) is methyl 3-((2RS)-2-{2-chloro-4-fluoro-5-[1,2,3,6-tetrahydro-3-methyl-2,6-dioxo-4-(trifluoromethyl)pyrimidin-1(6H)-yl]phenylthio}propionamido]propionate.

As for compound B, flazasulfuron (common name) is 1-(4,6-dimethoxypyrimidin-2-yl)-3-(3-trifluoromethyl-2-pyridylsulfonyl)urea.

The mixing ratio of compound A to compound B cannot generally be defined, since it varies depending upon various conditions such as the type of the formulation, the weather conditions, and the type and the growth stage of the undesired plants, and is preferably from 500:1 to 1:100 by the weight ratio, preferably from 50:1 to 1:33.3, more preferably from 20:1 to 1:10, still further preferably from 8:1 to 1:2.

The herbicidally effective amounts of compound A and compound B cannot generally be defined, since they vary depending upon various conditions such as the mixing ratio of compound A to compound B, the type of the formulation, the weather conditions, and the type and the growth stage of the undesired plants. For example, the herbicidally effective amount of compound A is from 5 to 500 g/ha, preferably from 7.5 to 250 g/ha, more preferably from 10 to 200 g/ha, still further preferably from 12.5 to 150 g/ha, and the herbicidally effective amount of compound B is from 1 to 500 g/ha, preferably from 5 to 250 g/ha, more preferably from 10 to 100 g/ha, further preferably from 20 to 40 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically cyperaceae such as green kyllinga (*Kyllinga brevifolia* Rottb. var. *leiolepis*), or sedge (*Cyperus* spp.) (such as purple nutsedge (*Cyperus rotundus* L.), smallflower umbrella sedge (*Cyperus difformis* L.), yellow nutsedge (*Cyperus esculentus* L.) or amur cyperus (*Cyperus microiria* Steud.)); gramineae such as barnyardgrass (*Echinochloa crus-galli* L., *Echinochloa oryzicola* vasing.), Japanese millet (*Echinochloa utilis* Ohwi et Yabuno)), crabgrass (*Digitaria* spp.) (such as summergrass (*Digitaria ciliaris* (Retz.) Koel), large crabgrass (*Digitaria sanguinalis* L.), violet crabgrass (*Digitaria violascens* Link) or jamaican crabgrass (*Digitaria horizontalis* Willd.)), green foxtail (*Setaria viridis* L.), goosegrass (*Eleusine indica* L.), johnsongrass (*Sorghum halepense* (L) Pers.), bermudagrass (*Cynodon dactylon* (L.) Pers.), wild oat (*Avena fatua* L.), annual bluegrass (*Poa annua* L.), panic grass (*Panicum* spp.) (such as guinea grass (*Panicum maximum* Jacq.) or fall panicum (*Panicum dichotomiflorum* (L.) Michx.)), signal grass (*Brachiaria* spp.) (such as plantain signal grass (*Brachiaria plantaginea* (LINK) Hitchc.), palisade signal grass (*Brachiaria decumbens* Stapf) or mauritius signal grass (*Brachiaria mutica* (Forssk.) Stapf)), paspalum (*Paspalum* spp.), itchgrass (*Rottboellia cochinchinensis* (LOUR.) W. D. CLAYTON)), southern sandbur (*Cenchrus echinatus* L.), shattercane (*Sorghum bicolor* (L.) Moench.), italian ryegrass (*Lolium multiflorum* Lam.), or cogon grass (*Imperata cylindrica* (L.) P. Beauv.); scrophulariaceae such as persian speedwell (*Veronica persica* Poir.) or corn speedwell (*Veronica arvensis* L.); compositae such as beggar ticks (*Bidens* spp.) (such as hairy beggarticks (*Bidens pilosa* L.), devils berggarticks (*Bidens frondosa* L.), *Bidens biternata* (Lour.) Merr. et Sherif or beggarticks (*Bidens subalternans* DC.)), hairy fleabane (*Conyza bonariensis* (L.) Cronq.)), horseweed (*Erigeron canadensis* L.), dandelion (*Taraxacum officinale* Weber), or common cocklebur (*Xanthium strumarium* L.); leguminosae such as rattlepod or rattlebox (*Crotalaria* spp.) (such as sunn-hemp (*Crotalaria juncea* L.)), poison bean (*Sesbania* spp.) (such as rostrate sesbania (*Sesbania rostrata* Bremek. & Oberm.) or sesbania pea (*Sesbania cannabina* (Retz.) Pers.)), or white clover (*Trifolium repens* L.)); caryophyllaceae such as sticky chickweed (*Cerastium glomeratum* Thuill.) or common chickweed (*Stellaria media* L.)); euphorbiaceae such as garden spurge (*Euphorbia hirta* L.), threeseeded copperleaf (*Acalypha australis* L.) or fireplant (*Euphorbia heterophylla* L.); plantaginaceae such as asiatic plantain (*Plantago asiatica* L.); oxalidaceae such as creeping woodsorrel (*Oxalis corniculata* L.): apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly sida (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea quamoclit* L.), *Ipomoea grandifolia* (DAMMERMANN) O'DONNELL, hairy merremia (*Merremia aegyptia* (L.) URBAN) or field bindweed (*Convolvulus arvensis* L.); chenopodiaceae such as common lambsquarters (*Chenopodium album* L.)); portulacaceae such as common purslane (*Portulaca oleracea* L.); amarinthaceae such as pigweed (*Amaranthus* spp.) (such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol.), powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.), ataco (*Amaranthus quitensis* Kunth.) or roughfruit amaranth (*Amaranthus rudis* Sauer.)): solanaceae such as black nightshade (*Solanum nigrum* L.)); polygonaceae such as spotted knotweed (*Polygonum lapathifolium* L.) or green smartweed (*Polygonum scabrum* MOENCH)); cruciferae such as flexuous bittercress (*Cardamine flexuosa* WITH.); cucurbitaceae such as burcucumber (*Sicyos angulatus* L.); commelinaceae such as common dayflower (*Commelina communis* L.); rosaceae such as mock strawberry (*Duchesnea chrysantha* (Zoll. et Mor.) Miq.); molluginacea such as carpetweed (*Mollugo verticillata* L.); rubiaceae such as false cleavers (*Galium spurium* var. echinospermon (Wallr.) Hayek) or stickywilly (*Galium aparine* L.); or equisetaceae such as common horsetail (*Equisetum arvense*).

The herbicidal composition of the present invention is particularly useful for controlling *Diqitaria* spp., commelinaceae or equisetaceae among the above undesired plants. More specifically, the herbicidal composition of the present invention is useful for controlling large crabgrass (*Diqitaria sanquinalis* L.), common dayflower (*Commelina communis* L.) or common horsetail (*Equisetum arvense*).

The herbicidal composition of the present invention is very useful in practical application. For example, the following may be mentioned.

(1) The herbicidal composition of the present invention has a remarkable synergistic effect, and has a favorable herbicidal activity even if the doses of the respective compounds A and B are small, and accordingly the impact on the surrounding environment can be suppressed.

(2) A herbicidal composition having a long lasting herbicidal effect i.e. a long lasting residual activity, as compared with a case where compound A or compound B is applied individually, may be provided in some cases.

(3) A herbicidal composition having a broad spectrum having high effects against both gramineae and broad leaf weeds, as compared with a case where compound A or compound B is applied individually, may be provided in some cases.

(4) Emergence of herbicide-resistant weeds and weeds having lowered sensitivity to herbicides, may be suppressed in some cases since compound A and compound B differing in the activity are combined.

(5) Safety for useful crop plants may be improved in some cases as compared with a case where compound A or compound B is applied individually.

In the herbicidal composition of the present invention, the following known herbicidal compounds (common names etc.) may be mixed if desired, Therefore, the range of weeds to be controlled, the time of application of the composition, the herbicidal activities, etc. may be improved to preferred directions. Even when not specifically mentioned here, in a case where such compounds have salts, alkyl esters, hydrates, different crystalline form, structural isomers etc., they are, of course, all included.

(1) Those which are believed to exhibit herbicidal effects by disturbing hormone activities of plants, such as phenoxy type compounds such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide and clomeprop; aromatic carboxylic acid type compounds such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium, aminopyralid, aminocyclopyrachlor and halauxifen; and other compounds such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol and chlorflurenol-methyl.

(2) Those which are believed to exhibit herbicidal effects by inhibiting photosynthesis of plants, such as urea type compounds such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton and trietazine; triazine type compounds such as simazine, atrazine, atratone, simetryn, prometryn, dimethametryn, hexazinone, metribuzin, terbuthylazine, cyanazine, ametryn, cybutryne, terbutryn, propazine, metamitron and prometon; uracil type compounds such as bromacil, bromacyl-lithium, lenacil and terbacil; anilide type compounds such as propanil and cypromid; carbamate type compounds such as swep, desmedipham and phenmedipham; hydroxybenzonitrile type compounds such as bromoxynil, bromoxynil-octanoate, bromoxynil-heptanoate, ioxynil, ioxynil-octanoate, ioxynil-potassium and ioxynil-sodium; and other compounds such as pyridate, bentazone, bentazone-sodium, amicarbazone, methazole, pentanochlor and phenmedipham.

(3) Quaternary ammonium salt type compounds such as paraquat and diquat, which are believed to be converted to free radicals by themselves to form active oxygen in the plant body and show rapid herbicidal efficacy.

(4) Those which are believed to exhibit herbicidal effects by inhibiting chlorophyll biosynthesis of plants and abnormally accumulating a photosensitizing peroxide substance in the plant body, such as diphenylether type compounds such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl and fluoroglycofen; cyclic imide type compounds such as chlorphthalim, flumioxazin, flumiclorac, flumiclorac-pentyl, cinidon-ethyl and fluthiacet-methyl; and other compounds such as oxadiargyl, oxadiazon, sulfentrazone, carfentrazone-ethyl, thidiazim in, pentoxazone, azafenidin, isopropazole, pyraflufen-ethyl, benzfendizone, butafenacil, saflufenacil, fluazolate, profluazol, flufenpyr-ethyl, bencarbazone and pyraclonil.

(5) Those which are believed to exhibit herbicidal effects characterized by bleaching activities by inhibiting chromogenesis of plants such as carotenoids, such as pyridazinone type compounds such as norflurazon, chloridazon and metflurazon; pyrazole type compounds such as pyrazolynate, pyrazoxyfen, benzofenap, topramezone and pyrasulfotole; and other compounds such as amitrole, fluridone, flurtamone, diflufenican, methoxyphenone, clomazone, sulcotrione, mesotrione, tembotrione, tefuryltrione, KUH-110, SW-065, isoxaflutole, difenzoquat, difenzoquat-metilsulfate, isoxachlortole, benzobicyclon, bicyclopyrone, picolinafen and beflubutam id.

(6) Those which are believed to exhibit herbicidal effects by inhibiting biosynthesis of fatty acid, such as aryloxyphenoxypropionic acid type compounds such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop and propaquizafop; cyclohexanedione type compounds such as alloxydim-sodium, alloxydim, clethodim, sethoxydim, tralkoxydim, butroxydim, tepraloxydim, profoxydim and cycloxydim; and phenylpyrazoline type compounds such as pinoxaden.

(7) Those which are believed to exhibit herbicidal effects by inhibiting an amino acid biosynthesis of plants, such as sulfonylurea type compounds such as chlorimuron-ethyl, chlorimuron, sulfometuron-methyl, sulfometuron, primisulfuron-methyl, prim isulfuron, bensulfuron-methyl, bensulfuron, chlorsulfuron, metsulfuron-methyl, metsulfuron, cinosulfuron, pyrazosulfuron-ethyl, pyrazosulfuron, rimsulfuron, nicosulfuron, imazosulfuron, flucetosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, amidosulfuron, azimsulfuron, propyrisulfuron, metazosulfuron, methiopyrsulfuron, monosulfuron-methyl and orsosulfuron; triazolopyrimidinesulfonamide type compounds such as flumetsulam, metosulam, diclosulam, cloransulam-methyl, florasulam, penoxsulam and pyroxsulam; imidazolinone type compounds such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl and imazapic; pyrimidinylsalicylic acid type compounds such as pyrithiobac-sodium, bispyribac-sodium, pyriminobac-methyl, pyribenzoxim, pyriftalid, pyrimisulfan and triafamone; sulfonylaminocarbonyltriazolinone type compounds such as flucarbazone, flucarbazone-sodium, propoxycarbazone-sodium, propoxycarbazone and thiencarbazone; and other compounds such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium and cinmethylin.

(8) Those which are believed to exhibit herbicidal effects by inhibiting cell mitoses of plants, such as dinitroaniline type compounds such as trifluralin, oryzalin, nitralin, pendimethalin, ethalfluralin, benfluralin, prodiamine, butralin and dinitramine; amide type compounds such as bensulide, napropamide, propyzamide and pronamide; organic phosphorus type compounds such as amiprofos-methyl, butamifos, anilofos and piperophos; phenyl carbamate type compounds such as propham, chlorpropham, barban and carbetamide; cumylamine type compounds such as daimuron, cumyluron, bromobutide and methyldymron; and other compounds such as asulam, asulam-sodium, dithiopyr, thiazopyr, chlorthal-dimethyl, chlorthal, diphenamid, flamprop-M-methyl, flamprop-M and flamprop-M-isopropyl.

(9) Those which are believed to exhibit herbicidal effects by inhibiting protein biosynthesis or lipid biosynthesis of plants, such as chloroacetamide type compounds such as alachlor, metazachlor, butachlor, pretilachlor, metolachlor, S-metolachlor, thenylchlor, pethoxamid, acetochlor, propachlor, dimethenamid, dimethenamid-P, propisochlor and dimethachlor; thiocarbamate type compounds such as molinate, dimepiperate, pyributicarb, EPTC, butylate, vernolate, pebulate, cycloate, prosulfocarb, esprocarb, thiobencarb, diallate, tri-allate and orbencarb; and other compounds such as etobenzanid, mefenacet, flufenacet, tridiphane, cafenstrole, fentrazamide, oxaziclomefone, indanofan, benfuresate, pyroxasulfone, fenoxasulfone, methiozolin, dalapon, dalapon-sodium, TCA-sodium and trichloroacetic acid.

(10) Those which are believed to exhibit herbicidal effects by inhibiting cellulose biosynthesis of plants, such as dichlobenil, triaziflam, indaziflam and flupoxam.

(11) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, ipfencarbazone, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(12) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras.*

The herbicidal composition of the present invention may be prepared by mixing compound A and compound B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A and compound B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the abovementioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight % of the active ingredients to such various additives in the herbicidal composition of the present invention may be from about 0.001:99.999 to about 95:5, preferably from about 0.005:99.995 to about 90:10.

As a method of applying the herbicidal composition of the present invention, a proper method can be employed among various methods depending upon various conditions such as the application site, the type of the formulation, and the type and the growth stage of the undesired plants, and for example, the following methods may be mentioned.

1. Compound A and compound B are mixed and formulated together, and the formulation is applied as it is.

2. Compound A and compound B are mixed and formulated together, and the formulation is diluted to a predetermined concentration with e.g. water, and as the case requires, a spreader (such as a surfactant, a vegetable oil or a mineral oil) is added for application.

3. Compound A and compound B are separately formulated, and the formulations are applied as they are.

4. Compound A and compound B are separately formulated, and as the case requires, the formulations are diluted to predetermined concentrations with e.g. water, and as the case requires, a spreader (such as a surfactant, a vegetable oil or a mineral oil) is added, and the formulations are applied.

5. Compound A and compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention will be described below, but the present invention is by no means restricted thereto.

(1) A herbicidal composition comprising (A) tiafenacil or its salt and (B) flazasulfuron or its salt.

(2) The herbicidal composition according to (1), wherein the mixing ratio of (A) to (B) is within a range of from 500:1 to 1:100 by the weight ratio.

(3) The herbicidal composition according to (1), wherein the mixing ratio of (A) to (B) is within a range of from 20:1 to 1:10 by the weight ratio.

(4) The herbicidal composition according to (1), wherein the mixing ratio of (A) to (B) is within a range of from 8:1 to 1:2 by the weight ratio.

(5) A method for controlling undesired plants or inhibiting their growth, which comprises applying a herbicidally effective amount of (A) tiafenacil or its salt and a herbicidally effective amount of (B) flazasulfuron or its salt to the undesired plants or to a place where they grow.

(6) The method according to (5), wherein (A) is applied in an amount of from 5 to 500 g/ha, and (B) is applied in an amount of from 1 to 500 g/ha.

(7) The method according to (5), wherein (A) is applied in an amount of from 10 to 200 g/ha, and (B) is applied in an amount of from 10 to 100 g/ha.

(8) The method according to (5), wherein (A) is applied in an amount of from 12.5 to 150 g/ha, and (B) is applied in an amount of from 20 to 40 g/ha.

EXAMPLES

Now, the present invention will be described in further detail with reference to Examples. However, the present invention is by no means restricted to such specific Examples.

Test Example 1

Upland field soil was put into a 1/1,000,000 ha vat, and seeds of large crabgrass (*Digitaria sanguinalis* L.) were sown. When the large crabgrass reached 7-leaf stage, predetermined amounts of an emulsifiable concentrate (EC formulation) containing tiafenacil prepared by a conventional method, water dispersible granules containing flazasulfuron as an active ingredient (WG formulation, tradename: SHIBAGEN DF manufactured by Ishihara Sangyo Kaisha, Ltd.), were diluted with water in an amount corresponding to 300 L/ha, and applied for foliar treatment by a small sprayer.

On the 24th day after treatment, the state of growth of the large crabgrass was visually observed to determine the growth inhibition rate in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate (%) of large crabgrass | |
|---|---|---|---|
| | | Measured value | Calculated value |
| Tiafenacil | 12.5 | 20 | — |
| | 25 | 30 | — |
| Flazasulfuron | 20 | 40 | — |
| Tiafenacil + Flazasulfuron | 12.5 + 20 | 70 | 52 |
| Tiafenacil + Flazasulfuron | 25 + 20 | 70 | 58 |

Test Example 2

Upland field soil was put into a 1/500,000 ha pot, and seeds of large crabgrass (*Digitaria sanguinalis* L.) were sown. On the next day, predetermined amounts of EC formulation containing tiafenacil as an active ingredient (the same as in Test Example 1) and WG formulation containing flazasulfuron as an active ingredient (the same as in Test Example 1) were diluted with water in an amount corresponding to 300 L/ha, and applied for soil treatment by a small sprayer.

On the 14th day after treatment, the state of growth of the large crabgrass was visually observed to determine the growth inhibition rate in accordance with the same evaluation standard as in Test Example 1. The growth inhibition rate (%) (measured value) and the growth inhibition rate (%) (calculated value) calculated by the Colby's formula are shown in Table 2.

TABLE 2

| Compound | Dose (g/ha) | Growth inhibition rate (%) of large crabgrass | |
|---|---|---|---|
| | | Measured value | Calculated value |
| Tiafenacil | 50 | 65 | — |
| Flazasulfuron | 20 | 60 | — |
| Tiafenacil + Flazasulfuron | 50 + 20 | 100 | 86 |

Test Example 3

An orchard field was compartmentalized into 0.5 square meter per test section. When common dayflower (*Commelina communis* L.) which naturally grew thereafter reached a height of from 35 to 40 cm, predetermined amounts of a microemulsion (ME formulation) containing tiafenacil prepared by a conventional method and WG formulation containing flazasulfuron as an active ingredient (the same as in Test Example 1) were diluted with water (in an amount corresponding to 300 L/ha) containing 0.5 vol % of an agricultural adjuvant (tradename: Destiny HC, manufactured by Winfield Solutions LLC.) and applied for foliar treatment by a small sprayer.

On the 23rd day after treatment, the state of growth of the common dayflower was visually observed to determine the growth inhibition rate in accordance with the same evaluation standard as in Test Example 1. The growth inhibition rate (%) (measured value) and the growth inhibition rate (%) (calculated value) calculated by the Colby's formula are shown in Table 3.

TABLE 3

| Compound | Dose (g/ha) | Growth inhibition rate (%) of common dayflower | |
|---|---|---|---|
| | | Measured value | Calculated value |
| Tiafenacil | 25 | 50 | — |
| | 50 | 60 | — |
| Flazasulfuron | 20 | 45 | — |
| | 40 | 40 | — |
| Tiafenacil + Flazasulfuron | 25 + 20 | 80 | 73 |
| | 50 + 20 | 85 | 78 |
| | 25 + 40 | 85 | 70 |
| | 50 + 40 | 87 | 76 |

Test Example 4

An orchard field was compartmentalized into 0.5 square meter per test section. When large crabgrass (*Digitaria sanguinalis* L.) which naturally grew thereafter reached a height of from 50 to 55 cm, predetermined amounts of ME formulation containing tiafenacil as an active ingredient (the same as in Test Example 3) and WG formulation containing flazasulfuron as an active ingredient (the same as in Test Example 1) were diluted with water (in an amount corresponding to 300 L/ha) containing 0.5 vol % of an agricultural adjuvant (tradename: Destiny HC, manufactured by Winfield Solutions LLC.) and applied for foliar treatment by a small sprayer.

On the 23rd day after treatment, the state of growth of the common dayflower was visually observed to determine the growth inhibition rate in accordance with the same evaluation standard as in Test Example 1. The growth inhibition rate (%) (measured value) and the growth inhibition rate (%) (calculated value) calculated by the Colby's formula are shown in Table 4.

TABLE 4

| Compound | Dose (g/ha) | Growth inhibition rate (%) of large crabgrass | |
|---|---|---|---|
| | | Measured value | Calculated value |
| Tiafenacil | 25 | 5 | — |
| | 50 | 5 | — |
| | 100 | 8 | — |
| Flazasulfuron | 40 | 33 | — |
| Tiafenacil + Flazasulfuron | 25 + 40 | 78 | 36 |
| | 50 + 40 | 78 | 36 |
| | 100 + 40 | 78 | 38 |

Test Example 5

An orchard field was compartmentalized into 0.5 square meter per test section, When common horsetail (*Equisetum arvense*) which naturally grew thereafter reached a height of from 15 to 20 cm, predetermined amounts of ME formulation containing tiafenacil as an active ingredient (the same as in Test Example 3) and WG formulation containing flazasulfuron as an active ingredient (the same as in Test Example 1) were diluted with water (in an amount corresponding to 300 L/ha) containing 0.5 vol % of an agricultural adjuvant (tradename: Destiny HC, manufactured by Winfield Solutions LLC.) and applied for foliar treatment by a small sprayer.

On the 23rd day after treatment, the state of growth of the common horsetail was visually observed to determine the growth inhibition rate in accordance with the same evaluation standard as in Test Example 1. The growth inhibition rate (%) (measured value) and the growth inhibition rate (%) (calculated value) calculated by the Colby's formula are shown in Table 5.

TABLE 5

| Compound | Dose (g/ha) | Growth inhibition rate (%) of common horsetail | |
|---|---|---|---|
| | | Measured value | Calculated value |
| Tiafenacil | 25 | 63 | — |
| | 50 | 63 | — |
| | 100 | 68 | — |
| | 150 | 55 | — |
| Flazasulfuron | 20 | 55 | — |
| | 40 | 53 | — |
| Tiafenacil + Flazasulfuron | 50 + 20 | 94 | 83 |
| | 100 + 20 | 92 | 86 |
| | 150 + 20 | 89 | 80 |
| | 25 + 40 | 96 | 83 |
| | 50 + 40 | 96 | 83 |
| | 100 + 40 | 96 | 85 |
| | 150 + 40 | 97 | 79 |

INDUSTRIAL APPLICABILITY

The present invention is useful for controlling undesired plants in agricultural and horticultural fields represented by weeds such as *Digitaria* spp., cormmelinaceae and equisetaceae, which are to be controlled or growth of which is to be inhibited, and is useful for inhibiting their growth.

The entire disclosure of Japanese Patent Application No. 2013-220680 filed on Oct. 23, 2013 including specification, claims and summary is incorporated herein by reference in its entirety.

The invention claimed is:

1. A herbicidal composition comprising (A) tiafenacil or its salt and (B) flazasulfuron or its salt, wherein the ratio of (A) to (B) is from 8:1 to 1:2 by weight.

2. A method for controlling undesired plants or inhibiting their growth, which comprises applying the herbicidal composition as defined in claim 1 to the undesired plants or to a place where they grow.

3. The method according to claim 2, wherein the undesired plants are *Digitaria* spp., Commelinaceae or Equisetaceae.

4. A method for controlling undesired plants or inhibiting their growth, which comprises applying a herbicidally effective amount of (A) tiafenacil or its salt and a herbicidally effective amount of (B) flazasulfuron or its salt to the undesired plants or to a place where they grow, wherein (A) is applied in an amount of from 5 to 500 g/ha, and (B) is applied in an amount of from 1 to 500 g/ha, wherein the ratio of (A) to (B) is from 8:1 to 1:2 by weight.

5. The method according to claim 4, wherein (A) is applied in an amount of from 10 to 200 g/ha, and (B) is applied in an amount of from 10 to 100 g/ha.

6. The method according to claim 4, wherein the undesired plants are *Digitaria* spp., Commelinaceae or Equisetaceae.

7. The method according to claim 5, wherein the undesired plants are *Digitaria* spp., Commelinaceae or Equisetaceae.

* * * * *